(12) United States Patent
Niu et al.

(10) Patent No.: US 7,148,402 B2
(45) Date of Patent: Dec. 12, 2006

(54) PROMOTION OF SOMATIC EMBRYOGENESIS IN PLANTS BY PGA37 GENE EXPRESSION

(75) Inventors: Qi-Wen Niu, New York, NY (US); Nam-Hai Chua, New York, NY (US)

(73) Assignee: Rockefeller University, New York, NY (US)

( * ) Notice: Subject to any disclaimer, the term of this patent is extended or adjusted under 35 U.S.C. 154(b) by 0 days.

(21) Appl. No.: 10/850,465

(22) Filed: May 21, 2004

(65) Prior Publication Data

US 2005/0262595 A1    Nov. 24, 2005

(51) Int. Cl.
*C12N 15/82* (2006.01)

(52) U.S. Cl. ........................ 800/290; 800/287
(58) Field of Classification Search ................ 800/295; 435/320.1; 536/23.1
See application file for complete search history.

(56) References Cited

U.S. PATENT DOCUMENTS

| | | | |
|---|---|---|---|
| 6,239,327 B1 | 4/1998 | Zaghmout et al. | |
| 6,784,340 B1 | 8/2004 | Aoyama et al. | |
| 2003/0082813 A1 | 5/2003 | Zuo et al. | |

OTHER PUBLICATIONS

Zuo et al. The Plant Journal. 2002. vol. 30(3), pp. 349-359.*
Qu et al. Accession No. AY550306. Date: Mar. 2004. Database: GENBANK.*
Bicknell et al, 2004, Plant Cell 16:S228-245.*
Aoyama, T. et al., A glucocorticoid-mediated transcriptional induction system in transgenic plants, The Plant Journal, 1997, vol. 11, No. 3, pp. 605-612.
Stracke, R., The R2R3-MYB gene family in *Arabidopsis thaliana*, Curr. Opin. Plant Biology, 2000, vol. 4, No. 5, pp. 447-456.
Zuo, Jianru et al., The WUSCHEL gene promotes vegetative-to-embryonic transition in *Arabidopsis*, The Plant Journal, 2002, vol. 30, No. 3, pp. 349-359.
AF334817, GenBank, *Arabidopsis thaliana* putative transcription factor, 2 pgs., Aug. 30, 2001.
AY550306, GenBank, *Arabidopsis thaliana* MYB transcription factor, 2 pgs., Mar. 16, 2004.
NM113694, GenBank, *Arabidopsis thaliana* myb family transcription factor, 2 pgs., Feb. 19, 2004.

* cited by examiner

*Primary Examiner*—Anne Kubelik
(74) *Attorney, Agent, or Firm*—Rothwell, Figg, Ernst & Manbeck (57) ABSTRACT

The present invention relates to methods for promoting somatic embryogenesis from a plant cell, tissue, organ, callus or cell culture, by overexpressing a PGA37 gene in the tissue or organ. In one embodiment, such overexpression can be used as a silent selectable marker for transgenic plants. In another embodiment, such expression can be used to confer apomixis to a plant. In another embodiment, such overexpression can be used to create haploid plants, which can be used to produce dihaploid plants.

65 Claims, 6 Drawing Sheets

```
atggagttcg agtcagtgtt caaaatgcat tatccgtatc tcgcagccgt tatctacgat
gatagctcca ctttaaaaga ttttcatcca tctcttaccg atgattttc ttgtgtacac
aatgtgcatc acaaaccatc gatgcctcac acatatgaaa taccatcaaa agaaaccatt
agggggcatca ctccttctcc atgcactgaa gctttcgggg catgttttca tggcacatcc
aacgaccatg ttttttttgg catggcctat accaccccac caactattga acccaacgtt
tcacatgtct cacatgacaa tactatgtgg gaaaacgatc aaaaccaagg attcatcttt
ggaaccgagt caaccctcaa tcaagccatg gcggactcta atcaattcaa tatgccaaaa
ccactcttga gcgcaaacga agacaccatc atgaatcgac gtcaaaataa ccaggtaatg
atcaagaccg agcagatcaa gaagaagaac aagagatttc agatgaggag gatatgtaaa
cccacaaaaa aagctagcat catcaaagga caatggactc ctgaagaaga caagttattg
gtgcagctag tggaccttca cggaactaaa aaatggtctc agattgctaa gatgcttcaa
ggacgagttg gaaaacagtg cagagaaagg tggcataacc atctccgtcc cgatatcaag
aaagatggat ggactgaaga agaggatata atactgataa aagcccataa ggagattggg
aacagatggg ctgagatagc tcgaaaactc ccgggacgca ctgaaaatac gatcaagaac
cattggaacg cgactaaacg tcgacaacac tcgaggagga ctaaaggaaa agatgaaatt
tcccttttcac ttggtagcaa cactcttcag aactacatta ggtctgttac ctacaatgat
gatcctttca tgaccgcaaa tgcaaacgca acattggtc caagaaacat gagaggtaaa
ggtaagaatg taatggttgc ggtctcggag tatgatgagg gtgaatgtaa gtatattgtg
gatggtgtga ataacttggg tttagaagat ggaaggatca agatgccgtc attggcggct
atgtcggcct ccggatcagc gtctacttct ggttctgcgt ctggttctgg aagtggtgtg
accatggaga ttgatgagcc gatgactgat agctggatgg tgatgcatgg atgtgatgaa
gttatgatga acgagattgc tttgctggag atgattgctc atggtcgtct ttag (SEQ ID
NO:1)
```

Fig. 5A

```
MEFESVFKMHYPYLAAVIYDDSSTLKDFHPSLTDDFSCVHNVHHKPSMPHTYEIPSKETI
RGITPSPCTEAFGACFHGTSNDHVFFGMAYTTPPTIEPNVSHVSHDNTMWENDQNQGFIF
GTESTLNQAMADSNQFNMPKPLLSANEDTIMNRRQNNQVMIKTEQIKKKNKRFQMRRICK
PTKKASIIKGQWTPEEDKLLVQLVDLHGTKKWSQIAKMLQGRVGKQCRERWHNHLRPDIK
KDGWTEEEDIILIKAHKEIGNRWAEIARKLPGRTENTIKNHWNATKRRQHSRRTKGKDEI
SLSLGSNTLQNYIRSVTYNDDPFMTANANANIGPRNMRGKGKNVMVAVSEYDEGECKYIV
DGVNNLGLEDGRIKMPSLAAMSASGSASTSGSASGSGSGVTMEIDEPMTDSWMVMHGCDE
VMMNEIALLEMIAHGRL (SEQ ID NO:2)
```

PROMOTION OF SOMATIC EMBRYOGENESIS IN PLANTS BY PGA37 GENE EXPRESSION

BACKGROUND OF THE INVENTION

Somatic embryogenesis is a unique pathway for asexual propagation or somatic cloning in plants. The developmental process of somatic embryogenesis shares considerable similarity with that of zygotic embryogenesis (Zimmerman, 1993; Mordhorst et al., 1997) and this is likely due to the conservation in the underpinning cellular and molecular mechanisms between the two processes. Therefore, somatic embryogenesis provides an attractive model system for studying zygotic embryogenesis, particularly because zygotic embryos are encased by maternal tissues and difficult to access by biochemical and molecular tools. Moreover, in biotechnological applications, most economically important crop as well as non-crop plants are regenerated via somatic embryogenesis.

In contrast to organogenesis, which requires a high cytokinin to auxin ratio (Skoog and Miller, 1957; Sugiyama, 1999; Sugiyama, 2000), somatic embryogenesis does not require any external cytokinins, but rather is dependent on high concentrations of 2,4-D (Zimmerman, 1993; Mordhorst et al., 1997; Sugiyama, 2000), a synthetic chemical that has long been used as a functional analog of auxin. It is generally believed that somatic embryogenesis is mediated by a signaling cascade triggered by external auxin or 2,4-D (Zimmerman, 1993; Mordhorst et al., 1997; Schmidt et al., 1997). However, very little is known about the signal transduction pathway, particularly the molecular mechanism involved in the transition of a vegetative cell to an embryogenic competent cell.

During the last two decades, considerable efforts have been made to identify genes with altered expression patterns during somatic embryogenesis (Schmidt et al., 1997; Lin et al., 1996; Thomas, 1993). Most of these genes, however, are up-regulated only in late developmental stages, suggesting that they do not play a direct role in the vegetative-to-embryogenic transition. Thus far, the only exception is the carrot Somatic Embryogenesis Receptor-like Kinase (SERK) gene the expression of which appears to mark the vegetative-to-embryogenic transition; however, its function remains unclear (Schmidt et al., 1997).

An additional molecular approach was attempted by manipulating certain embryo-specific genes. The *Arabidopsis* Leafy cotyledon 1 (LEC1) gene, encoding a subunit of the HAP heterotrimeric transcription factor complex (HAP3), has been proposed as a key regulator for embryonic identity (Lotan et al., 1998). Mutations in the LEC1 locus result in defective embryo maturation as well as the conversion of cotyledons into true-leaf-like structures (Lotan et al., 1998; Meinke, 1992; Meinke et al., 1994). Constitutive overexpression of LEC1 leads to severely abnormal plant growth and development with occasional formation of somatic embryo-like structures (Lotan et al., 1998). The developmental fate of these embryo-like structures, however, remained unknown due to the lethality of LEC1 overexpression.

Another LEC gene, LEAFY COTYLEDON2 (LEC2), encodes a B3 domain transcription factor that acts primarily in developing seeds. Ectopic post-embryonic expression of LEC2 in transgenic plants induces the formation of somatic embryo-like and other organ-like structures and often confers embryonic characteristics to seedlings (Stone et al., 2001).

The *Brassica napus* BABY BOOM (BBM) gene encodes a member of the AP2/ERF transcription factor family, which is preferentially expressed during development of embryos and seeds (Boutilier et al., 2002). Ectopic expression of BBM in *Arabidopsis* and Brassia led to the formation of somatic embryo-like structures and cotyledon-like structures on seedlings (Boutilier et al., 2002). It should be pointed out that in all these case, it is not known whether the somatic-embryo-like structures can germinate into fertile plants.

Using a novel chemical-inducible activation tagging system Zuo et al (2002) identified the PGA6 gene, which can promote vegetative-to-embryogenic transition in *Arabidopsis* roots and other organs. DNA sequence analysis of the PGA6 gene identified it as corresponding to the WUSCHEL (WUS) gene (Endirzzi et al., 1996; Laux et al., 1996; Mayer et al., 1998). Significantly, somatic embryos formed by WUS/PGA6 over-expression can germinate into fertile plants upon inducer withdrawal (Zuo et al., 2002).

The publications and other materials used herein to illuminate the background of the invention, and in particular, cases to provide additional details respecting the practice, are incorporated herein by reference, and for convenience, are referenced by author and date in the text and respectively grouped in the appended Bibliography.

SUMMARY OF THE INVENTION

One aspect of the present invention is a method to promote somatic embryogenesis from a plant cell, tissue, organ, callus or cell culture, the method comprising overexpressing a PGA37 gene in said tissue or organ.

A second aspect of the invention is a method to generate somatic plant embryos wherein the method comprises overexpressing a PGA37 gene in a plant cell, tissue, organ, callus or cell culture.

Another aspect of the invention is a method for generating shoots from a plant cell, tissue, organ, callus or cell culture, the method comprising overexpressing a PGA37 gene in said tissue or organ.

Yet another aspect of the invention is a method of selecting plants transformed with a vector comprising a silent selectable marker wherein the marker is a PGA37 gene.

Another object of the invention is a method of producing an apomictic plant line.

Another object of the invention is a method of producing haploid plants.

Another object of the invention is a method of producing seedless fruits.

BRIEF DESCRIPTION OF THE DRAWINGS

FIGS. 2A–2F illustrate the pga37 gain-of-function mutant phenotype. Root explants derived from pga37 seedlings were cultured on the non-inductive SCM (SCM minus 17-β-estradiol; SCM–) for 2 weeks (FIG. 2A) or on the inductive SCM (SCM plus 17-β-estradiol; SCM+) for 2 weeks (FIG. 2B). Note the somatic embryo-like callus in FIG. 2B.

FIG. 5A shows the nucleotide sequence of the pga37 cDNA (SEQ ID NO:1).

FIG. 5B shows the amino acid sequence of the pga37 protein (SEQ ID NO:2).

FIGS. 7A–7D show that overexpression of MYB118 gene is responsible for the phenotype of pga37.

FIGS. 8A and 8B show that root explants of pER10/PGA37 placed on SCM+ medium were able to generate somatic embryos.

FIGS. 9A–9B show that a knock-out mutant of PGA37 is defective embryo development.

DETAILED DESCRIPTION OF THE INVENTION

The following definitions are used herein.

"Plant cell" is the structural and physiological unit of plants, consisting of a protoplast and the cell wall.

"Plant tissue" is a group of plant cells organized into a structural and functional unit.

"Plant organ" is a collection of tissues which performs a particular function or set of functions in an plant's body. The leaf, stem, and root are three organs found in many plants. Organs are composed of tissues.

"Plant callus" is a cluster of undifferentiated plant cells that have the capacity to regenerate a whole plant in some species.

"Plant cell suspension culture" is an artificial procedure of growing plant cells. Cells are isolated from a callus induced in tissue explants of specific parts of a plant and are cultured in liquid medium.

"Plant cell culture" is a generic description which involves plant protoplast, plant cell, plant tissue, plant organ and plant culture, where these various types of culture involve, as a common factor, the growth of microbe-free plant material in an aseptic (sterile) environment, such as sterilized nutrient medium.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transferred nucleic acid fragments are referred to as "transgenic" or "transformed" organisms.

A "transgene" is a recombinant DNA construct that has been introduced into the genome by a transformation procedure.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises an isolated polynucleotide operably linked to at least one regulatory sequence. The term also embraces an isolated polynucleotide comprising a region encoding all or part of a functional RNA and at least one of the naturally occurring regulatory sequences directing expression in the source (e.g., organism) from which the polynucleotide was isolated.

To dissect the signaling pathway during somatic embryogenesis, we have employed a genetic approach to identify gain-of-function mutations that can promote embryogenic callus formation from *Arabidopsis* root explants. *Arabidopsis thaliana* is known to be a species difficult for somatic embryogenesis. Thus far, embryogenic calli could only be induced from immature embryos of wild-type (WT) plants or from the primordia timing (pt) mutant plant (Wu et al., 1992; Mordhorst et al., 1998; and references therein). Therefore, *Arabidopsis* vegetative explants appear to be reliable materials for screening for genetic mutations involved in the vegetative-to-embryonic transition.

Herein we disclose the identification of the Plant Growth Activator 37 (PGA37) gene by a novel genetic screen aimed at elucidating the molecular mechanism of somatic embryogenesis. An inducible gain-of-function mutation at this locus causes a rapid transition from vegetative or somatic to embryonic cells, leading to somatic embryo development from various tissues and organs. In the presence of inducer, overexpression of PGA37 promotes the formation of somatic embryos from vegetative tissues. Upon withdrawal of the inducer, these somatic embryos are able to germinate and grow into healthy, fertile plants. Moreover, loss-of-function of PGA37 in a T-DNA insertion line and reduction-of function of PGA37 in transgenic PGA37RNAi plants lead to a block in zygotic embryo development: Together, these results provide evidence that PGA37 is involved in the maintenance of embryonic cell identity and is critical and necessary for embryo development. PGA37 was found to be identical to the MYB118 (At3g27785.1) gene, a putative transcription factor (Stracke et al., 2001). The nucleic acid and protein sequences of MYB118 are those as shown by GenBank Accession Nos. AY550306, AF334817 and NM_113694. Our results reveal the function of MYB118/PGA37 during embryogenesis, and also open a new avenue in biotechnological applications.

Wu et al. (1992) previously reported the generation of somatic embryos from isolated *Arabidopsis* zygotic embryos at very low efficiency, which involved tedious multiple subculturing and hormone treatments. Our finding that the simple manipulation of a single gene (MYB118) was able to generate somatic embryos at very high frequency is a major advance in plant biotechnology. Our observation that MYB118 is capable of promoting vegetative-to-embryonic transition and eventually somatic embryo formation uncovers an additional critical function of this transcription factor during embryogenesis.

Recently, it was reported that Leafy cotyledon 2 (LEC2) encodes a transcription factor containing a B3 domain unique to several other plant transcription factors including ABI3/VP1 and FUS3. Overexpression of LEC2 leads to formation of somatic embryos as well as the formation of callus, cotyledon-like and leaf-like structures. The LEC2 gene is a central embryonic regulator that plays a critical role in both early and late embryogenesis (Stone et al., 2001). As shown in the Examples below, PGA37 was able to activate LEC2 expression.

In another embodiment of the invention, embryogenesis is induced in haploid cells, such as pollen cells, to produce haploid plants. This can be achieved by stably transforming a plant cell or tissue with a MYB118 gene under the control of a tissue-specific promoter that is active in a haploid cell or tissue, and expressing the MYB118 gene therein, or by introducing the MYB118 gene into a plant tissue or cell under the control of an inducible promoter and applying the inducer to cause expression of the MYB118 gene therein. In a preferred embodiment, the MYB118 gene is under the control of a promoter that is both haploid-tissue-specific and inducible. In a preferred embodiment, a promoter is used that is both inducible and tissue-specific, giving greater control over the process. In a most preferred embodiment, a MYB118 gene linked to an inducible pollen-specific promoter is used to induce somatic embryogenesis in pollen cells.

Expression of the gene in the haploid tissue or cell (for example, by application of the inducer specific for the inducible promoter) results in the formation of haploid somatic embryos, which can be grown into haploid plants using standard techniques. When an inducible promoter is used (whether tissue-specific or not), a preferred method comprises exposing excised transgenic tissue containing the haploid cells (e.g., pollen or ovules) to the inducer specific for the inducible promoter for a time sufficient to induce the formation of a somatic embryo, withdrawing the inducer, and growing the somatic embryo into a transgenic haploid plant in the absence of the inducer.

Diploidization of the haploid plants to form dihaploids, either spontaneously or by treatment with the appropriate chemical (e.g. colchicine) will significantly expedite the process of obtaining homozygous plants as compared to a method of conventional genetic segregation. This technology will not only be beneficial for breeding purposes but also for basic research such as studies of mutagenesis and other genetic studies, because dihaploids are truly homozygous down to the DNA level, containing two identical copies of each gene.

Additionally, MYB118 genes will be useful for inducing apomixis into plants. Apomixis and methods of conferring apomixis into plants are discussed in several patents (see, e.g., U.S. Pat. Nos. 5,710,367; 5,811,636; 6,028,185; 6,229,064; and 6,239,327 as well as WO 00/24914 which are incorporated herein by reference). Reproduction in plants is ordinarily classified as sexual or asexual. The term apomixis is generally accepted as the replacement of sexual reproduction by various forms of asexual reproduction (Rieger et al., 1976). In general the initiation of cell proliferation in the embryo and endosperm are uncoupled from fertilization. Apomixis is a genetically controlled method of reproduction in plants where the embryo is formed without union of an egg and a sperm. There are three basic types of apomictic reproduction: 1) apospory-embryo develops from a chromosomally unreduced egg in an embryo sac derived from a somatic cell in the nucellus, 2) diplospory-embryo develops from an unreduced egg in an embryo sac derived from the megaspore mother cell, and 3) adventitious embryony-embryo develops directly from a somatic cell. In most forms of apomixis, pseudogamy or fertilization of the polar nuclei to produce endosperm is necessary for seed viability. These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. Apomixis can make hybrid development more efficient. It also simplifies hybrid production and increases genetic diversity in plant species with good male sterility.

It would be ideal to find genes controlling obligate or a high level of apomixis in the cultivated species and be able to readily hybridize cross-compatible sexual x apomictic genotypes to produce true-breeding $F_1$ hybrids. In reality, most desirable genes controlling apomixis are found in the wild species which are distantly related to the cultivated species. Although interspecific crosses may be possible between the cultivated and wild species, chromosome pairing between genomes is usually low or nonexistent.

Although apomixis is effectively used in Citrus to produce uniform and disease- and virus-free rootstock (Parlevliet et al., 1959) and in buffelgrass (Bashaw, 1980) and Poa (Pepin et al., 1971) to produce improved cultivars, it has not been successfully transferred to a cultivated crop plant. The transfer of apomixis to important crops would make possible development of true-breeding hybrids and commercial production of hybrids without a need for cytoplasmic-nuclear male sterility and high cost, labor-intensive production processes. An obligately apomictic $F_1$ hybrid would breed true through the seed indefinitely and could be considered a vegetative or clonal method of reproduction through the seed. The development of apomictically reproducing cultivated crops would also provide a major contribution toward the food security in developing nations (Wilson et al., 1992).

A further aspect of the present invention is the production of seedless fruits. Seedless fruits are produced by knocking out or inhibiting the function of PGA37. Transgenic plants with knocked out PGA37 function do not produce seeds, but do produce fruits that will develop into seedless fruits. The methods of interfering with gene function in a transgenic plant include introducing a synthetic gene that causes sense or antisense suppression of the target gene (Taylor and Jorgensen, 1992). The suppression methods require substantial similarity between the target gene and the suppressing gene, greater than 80% nucleotide sequence identity (Mol et al., 1995). An additional method of interfering with gene function in a transgenic plant is the use of ribozymes. The expression of ribozymes in plant cells was described e.g. by Feyter et al. (1996). A further method for interfering with gene function in a transgenic plant is the use of interfering RNA (RNAi). For a description of RNAi gene suppression in plants by transcription, see U.S. Pat. No. 6,506,559, U.S. Patent Application Publication No. 2002/0168707 A1 and International patent application publication Nos. WO 98/53083, WO 99/53050 and WO 99/61631.

The present invention is further detailed in the following Examples, which are offered by way of illustration and are not intended to limit the invention in any manner. Standard techniques well known in the art or the techniques specifically described below are utilized.

EXAMPLE 1

Plant Materials, Growth Conditions and Plant Transformation

The Wassilewskija, Columbia and Landsberg ecotypes of A. thaliana were used. Plants were grown under continuous white light at 22° C. on solid A medium (1×MS salts (Murashige and Skoog, 1962), 3% sucrose, 0.8% agar) supplemented with appropriate antibiotics and/or the inducer 17-β-estradiol (10 uM). In planta transformation of Arabidopsis plants (the Columbia ecotype) was performed as described by Bechtold et al. (1993). Transformation of root explants was carried out according to Koncz et al. (1989).

EXAMPLE 2

Molecular Manipulations

Figure 1:
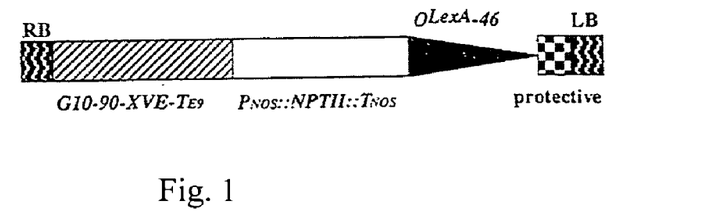
FIG. 1 is a schematic diagram of the XVE activation tagging vector pER16.

Molecular manipulations were performed as specifically stated or by the methods as taught by Sambrook et al. (1989). The XVE inducible expression vector pER10 is identical to pER8 (Zuo et al., 2000a) except that the hygromycin selectable marker of pER8 was replaced with a kanamycin selectable marker. To construct the mutagenesis vector pER16, pER10 was digested with SpeI and Asp718I followed by Klenow enzyme fill-in reaction and religation. The resulting pER16 vector lacked the rbcsS3A polyA addition sequence of the $O^{LexA-46}::T^{3A}$ expression cassette (Zuo et al. (2000a)).

pER16 is shown in FIG. 1. Only the region between the Right Border (RB) and Left Border (LB) is shown (not to scale). Two transcription units and the $O^{LexA}$-46 promoter are located between the RB and LB. In the first transcription unit, the G10-90 promoter (Ishige et al., 1999) drives the XVE fusion gene terminated by the rbcs E9 polyA addition sequence. The second transcription unit consists of the Nopaline Synthase (NOS) gene promoter, the coding sequence of the Neomycin Phosphotransferase II (NPT II) gene and the NOS polyadenylation sequence. The $O^{LexA}$-46 promoter consists of 8 copies of the LexA operator sequence fused to the −46 CaMV35S promoter. Upon integration into the plant genome, the $O^{LexA}$-46 promoter can activate the transcription of sequences fused downstream from the promoter in a 17-β-estradiol-dependent fashion.

The pER16-tagged genomic sequences were recovered by Tail-PCR (Liu et al., 1995), and the purified PCR fragments were directly subjected to DNA sequencing analysis.

The PGA37 cDNA was amplified from total RNA extracted from pga37 seedlings grown on MS medium with 17-β-estradiol (10 uM) by RT-PCR, using the primers MYB118Up (5'-AATAGGCGCGCCATGGAGTTCGAGT-CAGTGTTCA-3'; SEQ ID NO:3) and MYB118Low (5'-AATAACTAGTCTAAAGACGACCATGAGCAATCA-3'; SEQ ID NO:4). The 1336-bp long PCR fragment, harboring the entire protein coding region, was cut with Asc1 (site in MYB1187Up primer) and SpeI (site in MYB118Low primer) for cloning into the corresponding sites of the pER10 vector (Zuo et al., 2000). The correct sequence of the MYB118 cDNA was confirmed by DNA sequencing analysis.

RNA Northern blotting analyses were carried out as previously described (Zuo et al., 2000a; Zuo et al., 2001).

EXAMPLE 3

Screening of pga Mutants

Explants derived from Arabidopsis vegetative tissues are known to be incapable of forming somatic embryos or embryogenic calli promoted by external plant hormones. We presumed that external hormones alone were incapable of activating key regulators of Arabidopsis necessary for vegetative-to-embryogenesis transition. With appropriate hormone treatments, gain-of-function mutations in these regulatory genes may activate the vegetative-to-embryonic transition. Such gain-of-function mutations, on the other hand, may also cause severe defects during subsequent plant growth and development. Therefore, if the expression of the mutated gene and/or the biological activity of related gene products is not appropriately controlled, it will be difficult to maintain the identified mutations. An example is the constitutive overexpression of the LEC1 gene (Lotan et al., 1998). As a consequence, we carried out the screen by using a previously developed chemical-inducible XVE system, which has been demonstrated to be stringently controlled and to be highly responsive to the inducer 17-β-estradiol, a mammalian hormone with no apparent physiological effects on plant growth and development (Zuo et al., 2000a). The use of an inducible promoter thus allows us to recover normal mutant plants by withdrawal of the inducer, even in the case that the gain-of-function mutation is lethal.

To identify gain-of-function mutants related to the embryogenesis pathway, we carried out a functional screen by using a 17-β estradiol inducible activation-tagging system (Zuo et al. 2000a). In this screen, Agrobacterium tumefactions ABI cells carrying the pER16 vector (responsive to the 17-β estradiol inducer; FIG. 1) were used to transform Arabidopsis thaliana wild type Wassilewskija root explants according to Koncz et al. (1989). Infected root explants were cultured in a screening medium with inducer (SCM+), which contains MS salts 4.3 g/l, 0.15 mg/l indol-3-acetic acid, 50 mg/l kanamycin, 10 g/sucrose, and 10 μM 17 -β-estradiol without any cytokinin. WT root explants were not able to generate neither somatic embryo nor shoots on the SCM+ medium. However, a 17-β estradiol inducible gain-of-function mutation may activate the embryogenesis pathway to generate somatic embryo; alternatively, an inducible gain-of-function mutation may activate cytokynin signaling to generate shoots. In a large-scale screen, we have recovered over 40 putative mutants, which displayed "embryogenic" or "shooty" phenotypes in the presence but not absence of the 17-β estradiol inducer. We collectively named these two classes of mutants as pga (plant growth activators) (Zuo et al. 2002). One mutant that shows typical somatic embryonic calli in primary screening has been named pga37.

EXAMPLE 4

The pga37 Gain-of-Function Mutation Promotes Somatic Embryo Development

Figure 2A:
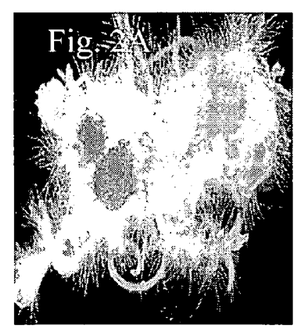
Figure 2B:
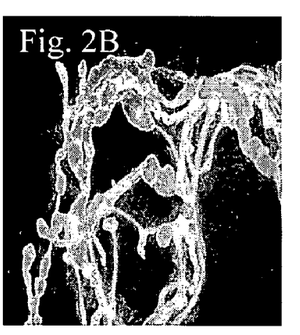
Figure 2C:
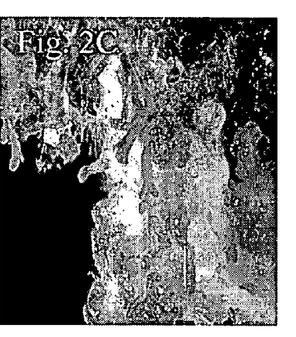
FIG. 2C shows that four-week old cultures of pga37 root explants on SCM+ regenerated somatic embryos.
Figure 2D:
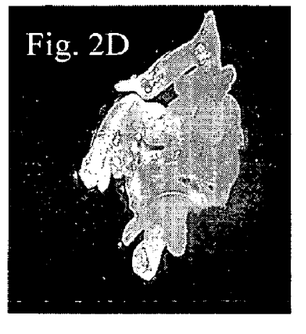
FIG. 2D shows an enlarged view of somatic embryos from FIG. 2C.
Figure 2E:
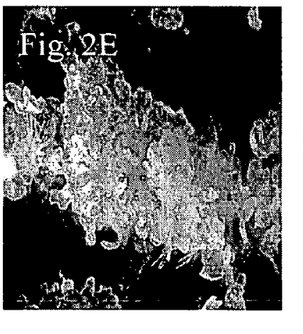
FIG. 2E shows that somatic embryos were able to germinate in a medium without the 17-β estradiol inducer.
Figure 2F:
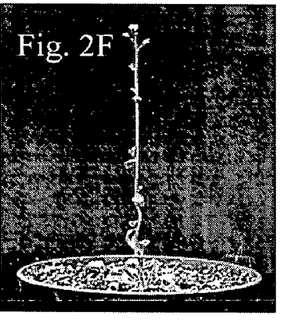
FIG. 2F shows that seedlings derived from somatic embryos were fertile and able to grow to maturity in soil and set seeds.

In primary screens, putative pga37 produced somatic embryo-like callus in SCM+ medium. Calli were transferred to a shoot regeneration medium to generate shoots, which were then transferred to a root regeneration medium for root regeneration. Shoots with roots were transferred to soil for growth to maturity in a growth chamber. To confirm whether the putative pga37 can promote somatic embryogensis, roots of pga37 T1 seedlings germinated on selection medium were collected and cultured on SCM+ or SCM without 17-β-estradiol (SCM−) as a negative control. After two weeks on SCM+ medium, the root explants produced yellow-green callus (FIG. 2B), which appeared like somatic embryogenic callus. After an additional two weeks of growth on SCM+ medium, regenerated somatic embryos were transferred to MS medium without 17-β-estradiol. These embryos germinated into seedlings, which subsequently developed into fertile adult plants and set seeds (FIGS. 2C–2F). By contrast, root explants which were cultured on SCM− medium produced roots and small normal calli because of the lower auxin concentration in the SCM− medium (FIG. 2A). No embryogenic calli were obtained in these cultures.

EXAMPLE 5

PGA37 Encodes a MYB-like DNA Biding Protein

Figure 3:
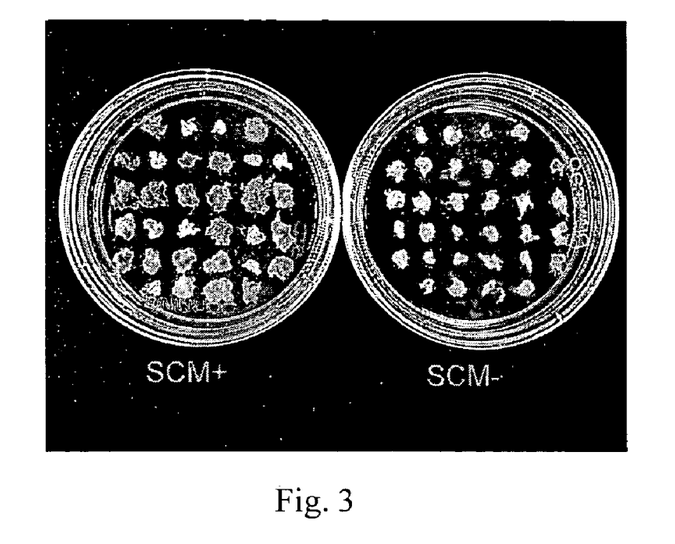
FIG. 3 shows a genetic analysis of the inducible mutant which showed that the 17-β-estradiol-dependent mutant phenotype and WT phenotype segregated in a ratio of 3:1, indicating that the inducible mutation was dominant in a single genetic locus. This result suggests the presence of one copy of T-DNA insert in the pga37 mutant.

Root explants collected from individual pga37 seedlings grown on MS medium without selection were cultured on both SCM+ and SCM− medium. Genetic analysis showed that the 17-β-estradiol-dependent mutant phenotype and WT phenotype segregated in a ratio of 3:1, indicating that the inducible mutation was dominant in a single genetic locus (FIG. 3). The segregation of antibiotic resistance marker in 3:1 ratio suggests the presence of one copy of T-DNA insert in the pga37 mutant.

Figure 4:
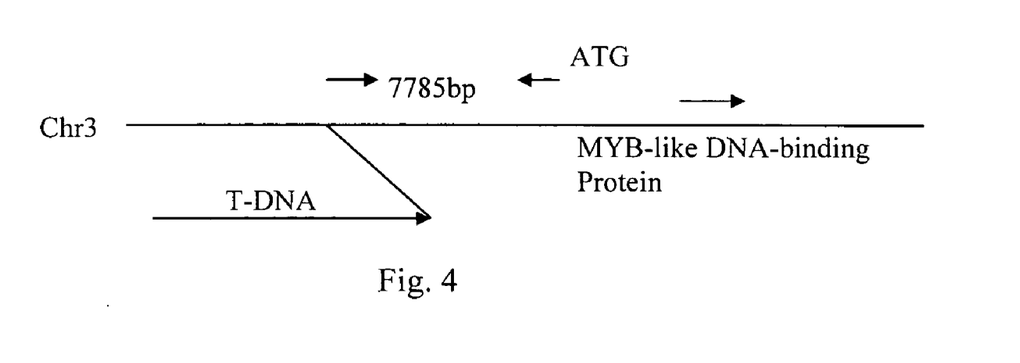
FIG. 4 shows the site of insertion of the T-DNA at 7,785 bp upstream of the putative translation start codon of the gene MYP118 (At3g27785.1).

Because the PGA37 gain-of-function phenotype was strictly dependent on the inducer, the PGA37 gene should be tagged by the 17-β estradiol inducible promoter of pER16 inserted in the pga37 genome. Taking advantage of this, we cloned the sequence downstream of the inducible promoter by Tail-PCR (Liu et al. 1995). Sequence analysis indicated that the T-DNA inserted 7,785 bp upstream from the putative translation start codon of the gene MYB118 (At3g27785.1) encoding a MYB-like DNA-binding protein (FIG. 4). The nucleotide sequence is shown in FIG. 5A (SEQ ID NO:1) and the amino acid sequences is shown in FIG. 5B (SEQ ID NO:2).

Figure 6:
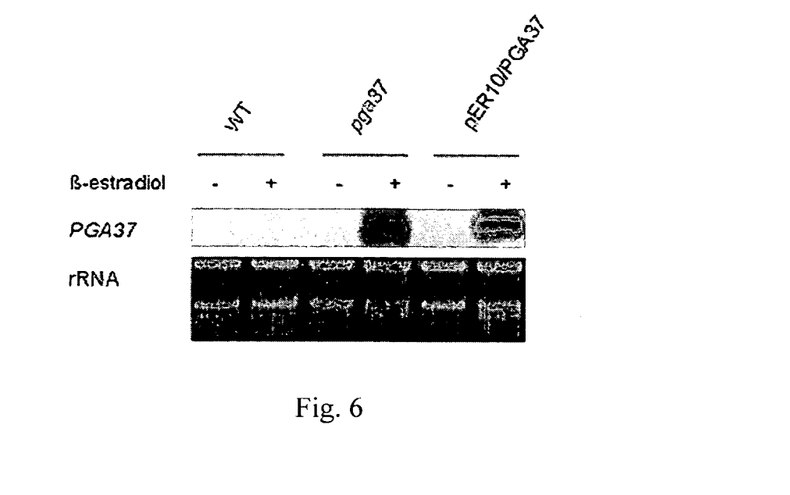
FIG. 6 shows a Northern blot analysis that demonstrates that the open reading frame encoding the MYB-like DNA binding protein was expressed only in the presence of inducer.

To verify whether MYB118 was activated by the inducible promoter, transcriptional level of this gene was analyzed by Northern blotting. FIG. 6 shows that the open reading frame encoding the MYB-like DNA-binding protein was expressed only in the presence of the inducer.

EXAMPLE 6

Figure 7A:
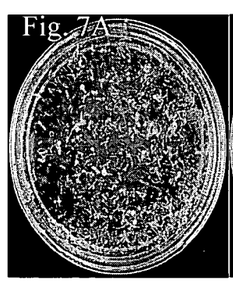
FIG. 7A shows root transformation on SCM− medium.
Figure 7B:
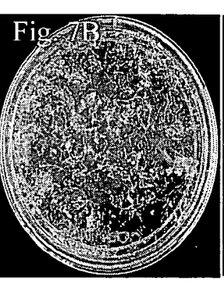
FIG. 7B shows root transformation on SCM+ medium.
Figure 7C:
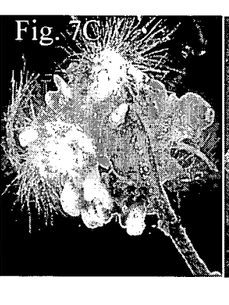
FIG. 7C shows an enlarged view of transformants showing the structure of somatic embryos.
Figure 7D:
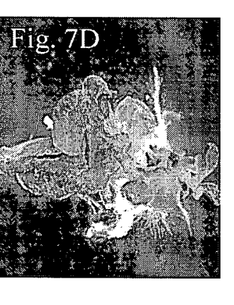
FIG. 7D shows that somatic embryos were transferred to MS medium without inducer medium.
Figure 8A:
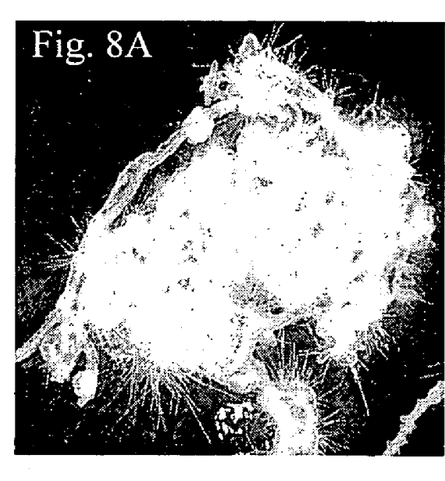
FIG. 8A shows culturing of roots of pER10/PGA37 transgenic T2 plants in SCM− medium.
Figure 8B:
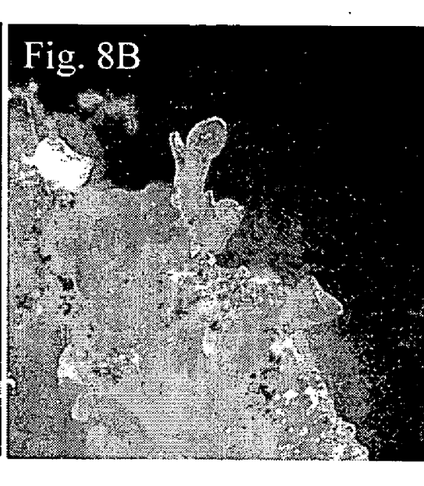
FIG. 8B shows roots of pER10/PGA37 transgenic T2 plants were cultured in SCM+ medium.

Somatic Embryo Formation of Explants Derived from Transgenic Plants Carrying a pER10-MYB118 Transgene The XVE vector pER10 is identical to pER8 except that the hygromycin resistance marker is replaced with a kanamycin-resistance marker (Zuo et al., 2000(a)). Full length MYB118 cDNA was placed under the control of the XVE system in pER10 (Zuo et al., 2001; Zuo et al., 2002). This construct was used to transform root explants from Arabidopsis wild type WS. Transformed roots explants were cultured on SCM+ medium, or SCM− medium as a negative control. Transformed root explants grown on SCM+ medium were able to generate somatic embryo after 3–4 weeks (FIGS. 7B and 7C) and these embryos were able to germinate when transferred to MS medium without the inducer (FIG. 7D). By contract, transformed root explants placed on SCM− medium were unable to produced somatic embryos (FIG. 7A). Root explants derived from T2 seedlings of pER10/PGA37 transgenic plants were cultured on SCM+ or SCM− medium. Similar to pga37, root explants of pER10/PGA37 placed only on SCM+ medium were able to generate somatic embryos (FIGS. 8A–8B).

EXAMPLE 7

A Knock-Out Mutant of PGA37 Has Defective Embryo Development

Figure 9A:
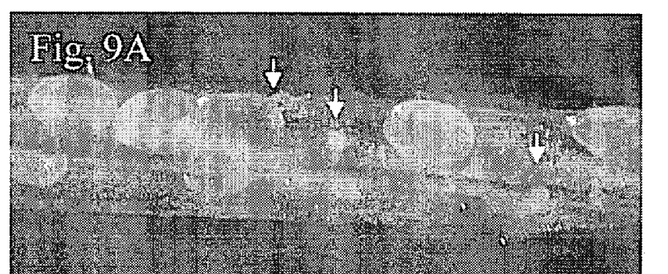
FIG. 9A shows that a knock-out mutant of PGA37 arrested embryo development at a very early stage of embryo development.
Figure 9B:
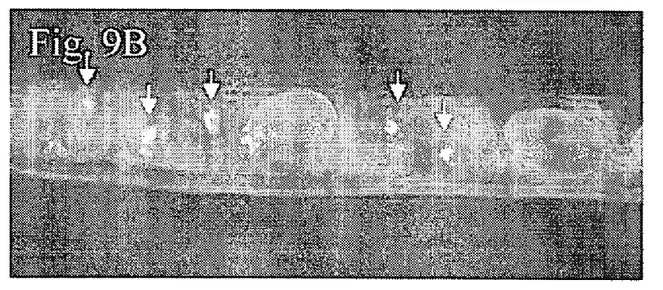
FIG. 9B shows that PGA37 RNAi transgenic lines showed the same embryo-lethal phenotype as the PGA37 knock-out mutant.

Knock-out phenotype is one of most important evidence for gene function. Phenotypic analysis of a PGA37 T-DNA insertion mutant (SALK_111,812) indicated that embryogenesis was either not activated or blocked at a very early stage in this mutant (FIG. 9A). A specific 396 bp (from nucleotide 4 to 400) 5'-terminal DNA fragment of PGA37 was used to produce an RNAi construct driven by a 35s promoter and used to transform Arabidopsis wild type Columbia ecotype plants. Several independent transgenic lines showed the same phenotype as that of the PGA37 T-DNA insertion mutant (FIG. 9B).

Figure 10:
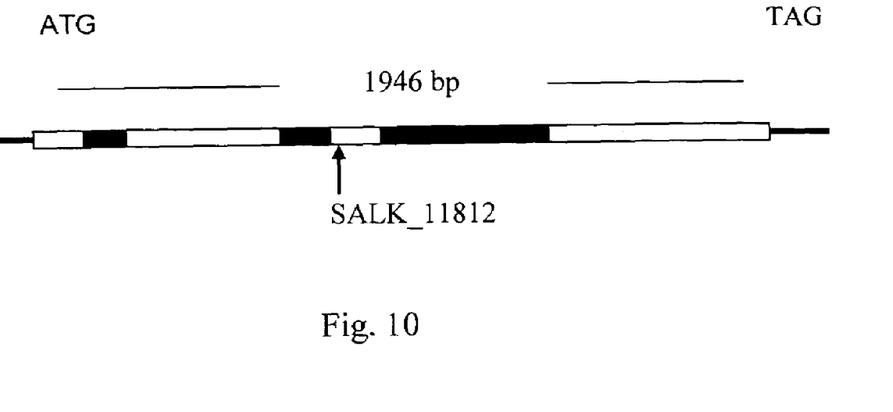
FIG. 10 shows that the T-DNA of the SALK_111812 mutant was inserted in 819 bp downstream from the putative translation start codon of the MYB118 gene. The open boxes represent exons and the black boxes represent introns.

FIG. 10 shows that the T-DNA of the SALK_111812 mutant was inserted in 819 bp downstream from the putative translation start codon of the MYB118 gene. The open boxes represent exons and the black boxes represent introns.

EXAMPLE 8

PGA37 Is Able to Activate the LEC2 Gene During Embryogenesis

Figure 11:
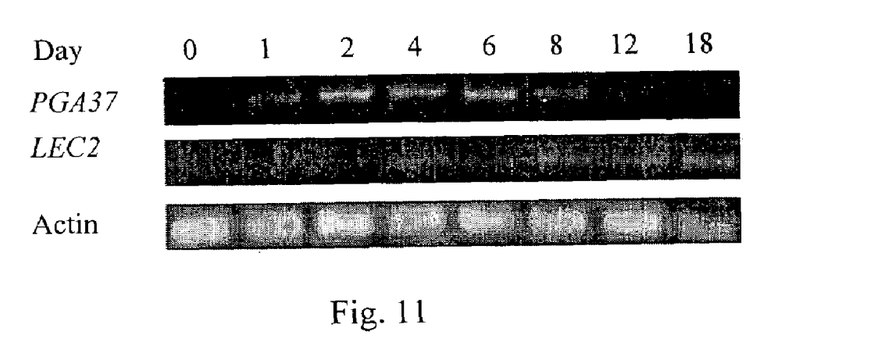
FIG. 11 shows that the PGA37 was able to activate LEC2 expression.

The Arabidopsis LEAFY COTYLEDON 2 (LEC2) gene is a central embryonic regulator that plays a critical role in both early and late embryogenesis (Stone et al. 2001). To verify the relationship between LEC2 and PGA37, roots explants of pga37 was cultured on SCM+ medium to induce somatic embryos. Total RNA was extracted at different time points. RT-PCR analysis indicated that PGA37 was able to active LEC2 expression (FIG. 11).

EXAMPLE 9

Placing MYB118 Under the Control of a Tissue-Specific Promoter

The G10-90 promoter in the XVE vector can be replaced with a tissue-specific promoter (e.g. a pollen-, root- stem- or leaf-specific promoter). A variety of tissue-specific promoters are well known to those of skill in the art. Because expression of a transgene is activated by the chimeric XVE gene which is controlled by a tissue-specific promoter in this Example, the $O^{lexA}$-46 promoter controlling the MYB118 transgene is therefore tissue-specific in an inducer-dependent manner. This means that MYB118 will be induced only in the presence of an inducer and only in the specific tissue corresponding to the tissue-specific promoter. Appropriate tissues or cell types, can then be collected from the transgenic plants and used for induction of somatic embryos as described in the above examples.

Particularly when pollen derived from transgenic plants carrying a pollen-specific promoter-XVE/$O^{lexA}$-46-MYB118 vector is used, progeny plants generated from pollen-derived somatic embryos should be haploid instead of diploid (see, e.g., Twell et al., 1989 and Twell et al., 1990 for pollen specific promoters). In this embodiment of the invention, a transgenic plant having in its genome a MYB118 gene under the control of an inducible, pollen-specific promoter would not normally express the gene. Pollen from such a plant can be cultured in the presence of the inducer until somatic embryogenesis occurs, after which the inducer is removed and the haploid embryos are permitted to develop into haploid clones according to standard techniques.

EXAMPLE 10

Use of the pER10-MYB118 as a Silent Marker for Transformation

The pER10-MYB118 vector can be used directly for transformation of explants without the use of an antibiotic resistance marker. Somatic embryos that formed in the presence of an inducer but in the absence of cytokinin should be transformants, because under such conditions non-transformants will be incapable of forming somatic embryos nor shoots due to the lack of induced MYB118 gene expression. Upon inducer removal, the embryos and shoots will develop into normal and fertile plants. The vector can include any gene or genes which are desired to be present in the transformed plants and these can be under the control of a desired promoter. The plants selected as a result of selecting for inducible MYB118 expression-dependent somatic embryos or shoots will contain the desired gene or genes.

If desired, the MYB118 transgene can be placed into a vector comprising a means of removing the MYB118 transgene as well as other portions of the vector which are no longer desired, e.g., using the XVE-Cre/lox system (Zuo et al., 2001). Such methods are also disclosed in U.S. Pat. No. 6,723,896, which is incorporated herein by reference.

EXAMPLE 11

Generating an Apomictic Plant

Apomixis can be induced by introducing MYB118 into a plant cell in such a manner that the MYB118 gene is expressed in the appropriate tissues (e.g., nucellus tissue). This can be by means of, but is not limited to, placing the MYB118 gene under the control of a tissue-specific promoter (e.g., a nucellus-specific promoter), an inducible promoter, or a promoter that is both inducible and tissue-specific. Inducing expression of the MYB118 gene, e.g. in the nucellus, produces apomixis leading to an apomictic plant. This plant may then be used to establish a true-breeding plant line. Additionally, the vector utilized to transfer MYB118 into the plant cell can include any other desired heterologous gene in addition to MYB118, including but not limited to, a marker gene or a gene to confer a desirable trait upon the plant, e.g., a gene resulting in larger plants, faster growth, resistance to stress, etc. This would lead to the development of an apomictic line with the desired trait.

In a variation of the scheme, plant expression cassettes, including but not limited to monocot or dicot expression cassettes, directing MYB118 expression to the inner integument or nucellus can easily be constructed. An expression cassette directing expression of the MYB118 DNA sequences to the nucellus is made using the barley Nuc1 promoter (Doan et al., 1996). The expression is used for plant transformation. Other genes which confer desirable traits can also be included in the cassette.

It is anticipated that transgenic plants carrying the expression cassette will then be capable of producing de novo embryos from MYB118 expressing nucellar cells. In the case of maize, this is complemented by pollinating the ears to promote normal central cell fertilization and endosperm development. In another variation of this scheme, transformations with a Nuc1:MYB118 expression cassette are done using a fie (fertility-independent endosperm)-null genetic background which would promote both de novo embryo development and endosperm development without fertilization (Ohad et al., 1999). Upon microscopic examination of the developing embryos it will be apparent that apomixis has occurred by the presence of embryos budding off the nucellus. In yet another variation of this scheme the MYB118 DNA sequences could be delivered as described above into a homozygous zygotic-embryo-lethal genotype. Only the adventive embryos produced from somatic nucellus tissue would develop in the seed.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

BIBLIOGRAPHY

Bashaw (1980). *Crop Science* 20:112.

Bechtold, N., Ellis, J., and Pelletier, G. (1993). "In planta Agrobacterium-mediated gene transfer by infiltration of adult *Arabidopsis thaliana* plants." *CR Acad Sci Ser III Sci Vie* 316:1194–1199.

Boutiller, K., Offringa, R., Sharma, V. K., Kieft, H., Ouellet, T., Zhang, L., Hattori, J., Liu, C.-M., Lammeren, A. A. M., Miki, B. L. A., Custers, J. B. M., and Campagne, M. M. L., (2002). "Ectopic espression of BABY BOOM triggers a conversion from vegetative to embryonic growth." *The Plant Cell* 14:1737–1749.

Doan, D. N., Linnestad, C. and Olsen, O. A. (1996). "Isolation of molecular markers from the barley endosperm coenocyte and the surrounding nucellus cell layers." *Plant Mol Biol* 31:877–886.

Endrizzi et al. (1996). *Plant Journal* 10:967–979.

Feyter et al. (1996). *Mol Gen Genet* 250:329–338.

Ishige, F., Takaichi, M., Foster, R., Chua, N.-H., and Oeda, K. (1999). "A G-box motif (GCCACGTGCC) tetramer confers high-level constitutive expression in dicot and monocot plants." *Plant J* 18:443–448.

Koncz, C., Martini, N., Mayerhofer, R., Koncz-Kalman, Z., Korber, H., Redei, G. P., and Schell, J. (1989). "High-frequency T-DNA-mediated gene tagging in plants." *Proc Natl Acad Sci USA* 86(21):8467–8471.

Laux et al. (1996). *Development* 122:87–96.

Lin, X., Hwang, G. J, and Zimmerman, J. L. (1996). "Isolation and characterization of a diverse set of genes from carrot somatic embryos." *Plant Physiol* 112:1365–1374.

Liu, Y. G., Mitsukawa, N., Oosumi, T., and Whittier, R. F. (1995). "Efficient isolation and mapping of *Arabidopsis thaliana* T-DNA insert junctions by thermal asymmetric interlaced PCR." *Plant J* 8:457–463.

Lotan, T., Ohto, M., Yee, K. M., West, M. A., Lo, R., Kwong, R. W., Yamagishi, K., Fischer, R. L., Goldberg, R. B., and Harada, J. J. (1998). "Arabidopsis LEAFY COTY- LEDON1 is sufficient to induce embryo development in vegetative cells." *Cell* 93:1195–1205.

Mayer et al. (1998). *Cell* 95:805–815.

Meinke, D. W., (1992). "A homoeotic mutant of *Arabidopsis thaliana* with leafy cotyledons." *Science* 258:1647–1650.

Meinke, D. W., Franzmann, L. H., Nickle, T. C., and Yeung, E. C. (1994). "Leafy cotyledon mutants of *Arabidopsis.*" *Plant Cell* 6:1049–1064.

Mol, J. M. N. et al. (1994). "Post-transcriptional inhibition of gene expression: sense and antisense genes." In: J. Paszkowski (Ed.). *Homologous Recombination and Gene Silencing in Plants*. Kluwer Academic Publishers. Dordrecht, Netherlands. pp. 309–334.

Mordhorst, A. P., Toonen, M. A. J., and de Vries, S. C. (1997). "Plant embryogenesis." *Crit Rev Plant Sci* 16:535–576.

Mordhorst, A. P., Voerman, K. J., Hartog, M. V., Meijer, E. A., van Went, J., Koornneef, M., and de Vries, S. C. (1998). "Somatic embryogenesis in *Arabidopsis thaliana* is facilitated by mutations in genes repressing meristematic cell divisions." *Genetics* 149:549–563.

Murashige, T., and Skoog, F. (1962). "A revised medium for rapid growth and bioassays with tobacco tissue culture." *Physiol Plant* 15:473–497.

Ohad, N., Yadegari, R., Margossian, L., Hannon, M., Michaeli, D., Harada, J. J., Goldberg, R. B., and Fischer, R. L. (1999). "Mutations in FIE, a WD polycomb group gene, allow endosperm development without fertilization." *The Plant Cell* 11:407–416.

Parlevliet, J. E. et al. (1959). "Citrus." *Proc Am Soc Hort Sci* 74: 252–260.

Pepin et al. (1971). *Crop Science* 11:445–448.

Rieger et al. (1976). In *Glossary of Genetics and Cytogenetics*, Springer-Verlag, New York, N.Y.

Sambrook, J., Fritsch, E. F., and Maniatis, T. (1989). *Molecular cloning: A Laboratory Manual*. 2$^{nd}$ Ed., Cold Spring Harbor, N.Y.: Cold Spring Harbor Laboratory Press.

Schmidt, E. D., Guzzo, F., Toonen, M. A., and de Vries, S. C. (1997). "A leucine-rich repeat containing receptor-like kinase marks somatic plant cells competent to form embryos." *Development* 124:2049–2062.

Skoog, F., and Miller, C. O. (1957). "Chemical regulation of growth and organ formation in plant tissues cultured in vitro." *Symp Soc Exp Biol* 11:118–131.

Stone, S. L., Kwong, L. W. Yee, K. M., Pelletier, J., Lepiniec, L., Fisher, R. L., Goldberg, R. B., and Harada, J. J. (2001). "LEAFY COTYLEDON 2 encodes a B3 domain transcription factor that induces embryo development." *Proc Natl Acad Sci USA* 98:11806–11811.

Stracke, R., Weber, M., and Weisshaar, B. (2001). The R2R3-MYB gene family in *Arabidopsis thaliana*. *Curr Opin Plant Biol* 4(5):447–456.

Sugiyama, M. (1999). "Organogenesis in vitro." *Curr Opin Plant Biol* 2:61–64.

Sugiyama, M. (2000). "Genetic analysis of plant morphogenesis in vitro." *Int Rev Cytol* 196:67–84.

Taylor, L. P. and Jorgensen, R. A. (1992). *J Hered* 83:11–17.

Thomas, T. L. (1993). "Gene expression during plant embryogenesis and germination: an overview." *Plant Cell* 5:1401–1410.

Twell, D., Wing, R. Yamaguchi, J. and McCormick S. (1989). "Isolation and expression of an anther-specific gene from tomato." *Mol Gen Genet* 217:240–245.

Twell, D. Yamaguchi, J. and McCormick, S. (1990). "Pollen-specific gene expression in transgenic plants: coordinate regulation of two different tomato gene promoters during microsporogenesis." *Development* 109:705–713.

Wilson et al. (1992). Proceedings of the International Workshop on Apomixis in Rice, Changsha, People's Republic of China, Jan. 13-Jan. 15, 1992. Hunan Hybrid Rice Research Center, Changsha, People's Republic of China.

Wu, Y., Haberland, G., Zhou, C., and Koop, H.-U. (1992). "Somatic embryogenesis, formation of morphogenetic callus and normal development in zygotic embryos of *Arabidopsis thaliana* in vitro." *Protoplasma* 169:89–96.

Zimmerman, J. L. (1993). "Somatic embryogenesis: A model for early development in higher plants." *Plant Cell* 5:1411–1423.

Zuo, J., Niu, Q.-W., and Chua, N.-H. (2000a). "An estrogen receptor-based transactivator XVE mediates highly inducible gene expression in transgenic plants." *Plant J* 24:265–273.

Zuo, J., Niu, Q.-W., Nishizawa, N., Wu, Y., Kost, B., and Chua, N.-H. (2000b). "KORRIGAN, an *Arabidopsis* endo-1,4-b-glucanase, localizes to the cell plate by polarized targeting and is essential for cytokinesis." *Plant Cell* 12(7): 1137–1152.

Zuo, J., Niu, Q.-W, Moller, S. G., and Chua, N.-H. (2001). "Chemical-regulated, site-specific DNA excision in transgenic plants." *Nat Biotechnol* 19.157–161.

Zuo, J., Niu, Q. W., Frugis, G., and Chua, N. H. (2002). "The WUSCHEL gene promotes vegetative-to-embryonic transition in *Arabidopsis.*" *Plant J* 30(3):349–59.

Published PCT Patent Application WO 98/53083
Published PCT Patent Application WO 99/53050
Published PCT Patent Application WO 99/61631
Published PCT Patent Application WO 00/24914.
Published PCT Patent Application WO 01/23575.
U.S. Patent Application Publication No. 2002/0168707 A1
U.S. Pat. No. 5,710,367
U.S. Pat. No. 5,811,636
U.S. Pat. No. 6,028,185
U.S. Pat. No. 6,229,064
U.S. Pat. No. 6,239,327
U.S. Pat. No. 6,506,559
U.S. Pat. No. 6,723,896

What is claimed is:

1. A method to promote somatic embryogenesis from a plant cell, tissue, organ, callus or cell culture, the method comprising expressing a nucleic acid encoding a PGA37 polypeptide having the amino acid sequence set forth in SEQ ID NO:2 in the plant cell, tissue, organ, callus or cell culture.

2. The method of claim 1, wherein the plant cell, tissue, organ, callus or cell culture comprises a promoter controlling expression of the nucleic acid encoding the PGA37 polypeptide.

3. The method of claim 2, wherein the plant cell, tissue, organ, callus or cell culture is transgenic for the promoter.

4. The method of claim 2, wherein the promoter is inducible.

5. The method of claim 1, wherein the nucleic acid encoding the PGA37 polypeptide which is expressed is in a vector.

6. The method of claim 5, wherein the vector comprises an inducible promoter controlling expression of the nucleic acid encoding the PGA37 polypeptide.

7. The method of claim 6, wherein the inducible promoter is inducible by an estrogen.

8. The method of claim 7, wherein the estrogen is 17-β-estradiol.

9. The method of claim 5, wherein the vector comprises a tissue-specific promoter.

10. The method of claim 1, wherein the plant is selected from the group consisting of trees and crops.

11. A method to generate plant somatic embryos wherein the method comprises expressing a nucleic acid encoding a PGA37 polypeptide having the amino acid sequence set forth in SEQ ID NO:2 in a plant cell, tissue, organ, callus or cell culture.

12. The method of claim 11, wherein the plant cell, tissue, organ, callus or cell culture comprises a promoter controlling expression of the nucleic acid encoding the PGA37 polypeptide.

13. The method of claim 12, wherein the plant cell, tissue, organ, callus or cell culture is transgenic for the promoter.

14. The method of claim 12, wherein the promoter is inducible.

15. The method of claim 11, wherein the nucleic acid encoding the PGA37 polypeptide which is expressed is in a vector.

16. The method of claim 15, wherein the vector comprises an inducible promoter controlling expression of the nucleic acid encoding the PGA37 polypeptide.

17. The method of claim 16, wherein the inducible promoter is inducible by an estrogen.

18. The method of claim 17, wherein the estrogen is 17-β-estradiol.

19. The method of claim 15, wherein the vector comprises a tissue-specific promoter.

20. The method of claim 11, wherein the plant is selected from the group consisting of trees and crops.

21. A method for generating shoots from a plant cell, tissue, organ, callus or cell culture, the method comprising expressing a nucleic acid encoding a PGA37 polypeptide having the amino acid sequence set forth in SEQ ID NO:2 in the plant cell, tissue, organ, callus or cell culture.

22. The method of claim 21, wherein the plant cell, tissue, organ, callus or cell culture comprises a promoter controlling expression of the nucleic acid encoding the PGA37 polypeptide.

23. The method of claim 22, wherein the plant cell, tissue, organ, callus or cell culture is transgenic for the promoter.

24. The method of claim 22, wherein the promoter is inducible.

25. The method of claim 21, wherein the nucleic acid encoding the PGA37 polypeptide which is expressed is in a vector.

26. The method of claim 25, wherein the vector comprises an inducible promoter controlling expression of the nucleic acid encoding the PGA37 polypeptide.

27. The method of claim 26, wherein the inducible promoter is inducible by an estrogen.

28. The method of claim 27, wherein the estrogen is 17-β-estradiol.

29. The method of claim 25, wherein the vector comprises a tissue-specific promoter.

30. The method of claim 21, wherein the plant is selected from the group consisting of trees and crops.

31. A method of selecting plants transformed with a vector comprising a silent selectable marker, the silent selectable marker being a nucleic acid encoding the PGA37 polypeptide having the amino acid sequence set forth in SEQ ID NO:2, the method comprising
  (a) transforming a plant, plant cell, tissue, organ, callus or cell culture with a vector comprising the nucleic acid encoding the PGA37 polypeptide under the control of an inducible promoter;
  (b) culturing the plant, plant cell, tissue, organ, callus or cell culture in the presence of an inducer of the inducible promoter;
  (c) selecting somatic embryos which form; and
  (d) growing the somatic embryos in the absence of the inducer to develop plants,
  wherein the plants which develop are transformed with the vector.

32. The method of claim 31, wherein the inducible promoter is inducible by an estrogen.

33. The method of claim 32, wherein the estrogen is 17-β-estradiol.

34. The method of claim 31, wherein the vector comprises a tissue-specific promoter.

35. The method of claim 31, wherein the vector comprises a gene of interest.

36. The method of claim 35, wherein the gene of interest is under the control of a promoter.

37. The method of claim 36, wherein the promoter controlling the gene of interest is a constitutive promoter or an inducible promoter.

38. The method of claim 31, wherein the plant plant cell, tissue, organ, callus or cell culture is selected from the group consisting of trees or crops.

39. The method of claim 31, wherein the vector comprises means for deleting the nucleic acid encoding the PGA37 polypeptide.

40. A method for inducing apomixis in a plant cell comprising expressing a nucleic acid encoding a PGA37 polypeptide having the amino acid sequence set forth in SEQ ID NO:2 in the plant cell.

41. The method of claim 40, wherein the plant cell is transformed with a vector comprising the nucleic acid encoding the PGA37 polypeptide.

42. The method of claim 41, wherein the nucleic acid encoding the PGA37 polypeptide is under the control of an inducible promoter.

43. The method of claim 41, wherein the vector comprises a second gene in addition to the nucleic acid encoding the PGA37 polypeptide.

44. The method of claim 43, wherein the second gene encodes a marker.

45. The method of claim 43, wherein the second gene confers a desired trait to the plant.

46. An apomictic plant comprising the nucleic acid encoding the PGA37 polypeptide under the control of an inducible promoter.

47. A method for conferring apomixis to a plant comprising
(a) stably transforming a responsive plant cell with a DNA sequence comprising at least one nucleic acid encoding a PGA37 polypeptide having the amino acid sequence set forth in SEQ ID NO:2 under the control of a promoter to produce a transgenic plant cell, the promoter being selected from the group consisting of a tissue-specific promoter, an inducible promoter and a promoter that is both tissue-specific and inducible,
(b) regenerating a transgenic plant from the transgenic plant cell,
whereby expression of the PGA37 polypeptide from the nucleic acid encoding the PGA37 polypeptide in the transgenic plant results in the formation of an apomictic embryo.

48. The method of claim 47, wherein the promoter is a tissue-specific promoter.

49. The method of claim 47, wherein the promoter is an inducible promoter.

50. The method of claim 47, wherein the promoter is both tissue-specific and inducible.

51. The method of claim 48, wherein the promoter is a nucellus-specific promoter.

52. The method of claim 48, wherein the transgenic plant cell comprises at least one additional heterologous DNA sequence in its genome.

53. A plant produced by the method of claim 47.

54. A method for producing a haploid plant comprising
(a) stably transforming a plant cell with a DNA sequence comprising at least one nucleic acid encoding a PGA37 polypeptide having the amino acid sequence set forth in SEQ ID NO:2 under the control of a promoter to produce a transgenic plant cell, wherein the promoter is selected from the group consisting of a haploid tissue-specific promoter, an inducible promoter and a promoter that is both haploid-tissue-specific and inducible,
(b) generating a transgenic plant from the transgenic plant cell,
(c) expressing the nucleic acid encoding the PGA37 polypeptide in a haploid tissue of the transgenic plant to produce a haploid somatic embryo,
(d) growing the embryo into a haploid plant.

55. The method of claim 54, wherein the promoter is a haploid tissue-specific promoter.

56. The method of claim 55, wherein the promoter is a pollen-specific promoter, and the haploid tissue of the transgenic plant is pollen.

57. The method of claim 55, wherein the promoter is an ovule-specific promoter, and the haploid tissue of the transgenic plant is ovule tissue.

58. The method of claim 54, wherein the promoter is an inducible promoter.

59. The method of claim 54, wherein the promoter is both haploid-tissue-specific and inducible.

60. The method of claim 58, wherein the promoter is pollen-specific, and the haploid plant cell is a pollen cell.

61. The method of claim 57, wherein the expressing step (c) is achieved in excised haploid tissue cultured in the presence of the inducer specific for the inducible promoter, for a time sufficient to induce formation of the haploid somatic embryo, followed by withdrawal of the inducer, and further wherein the growing step (d) is carried out in the absence of the inducer.

62. A method for producing seedless fruits comprising
(a) stably transforming a responsive plant cell with a nucleic acid comprising at least one DNA sequence under the control of a promoter to produce a transgenic plant cell, wherein the DNA sequence is capable of interfering with the expression of a nucleic acid encoding a PGA37 polypeptide having the amino acid sequence set forth in SEQ ID NO:2 and the promoter being selected from the group consisting of a tissue-specific promoter, an inducible promoter and a promoter that is both tissue-specific and inducible;
(b) regenerating a transgenic plant from the transgenic plant cell; and
(c) growing the transgenic plant under conditions that are suitable for the expression of the DNA sequence;
whereby expression of the DNA sequence interferes with the expression of the nucleic acid encoding a PGA37 polypeptide in the transgenic plant and results in the formation of a seedless fruit.

63. The method of claim 62, wherein the promoter is an inducible promoter.

64. The method of claim 63, wherein the inducible promoter is inducible by an estrogen.

65. The method of claim 64, wherein the estrogen is 17-β-estradiol.

* * * * *

SEQUENCE LISTING

```
<160> NUMBER OF SEQ ID NOS: 4

<210> SEQ ID NO 1
<211> LENGTH: 1314
<212> TYPE: DNA
<213> ORGANISM: Arabidopsis thaliana
```

<220> FEATURE:
<221> NAME/KEY: CDS
<222> LOCATION: (1)..(1314)

<400> SEQUENCE: 1

| | |
|---|---|
| atg gag ttc gag tca gtg ttc aaa atg cat tat ccg tat ctc gca gcc<br>Met Glu Phe Glu Ser Val Phe Lys Met His Tyr Pro Tyr Leu Ala Ala<br>1                      5                    10                 15 | 48 |
| gtt atc tac gat gat agc tcc act tta aaa gat ttt cat cca tct ctt<br>Val Ile Tyr Asp Asp Ser Ser Thr Leu Lys Asp Phe His Pro Ser Leu<br>                  20                    25                  30 | 96 |
| acc gat gat ttt tct tgt gta cac aat gtg cat cac aaa cca tcg atg<br>Thr Asp Asp Phe Ser Cys Val His Asn Val His His Lys Pro Ser Met<br>        35                    40                    45 | 144 |
| cct cac aca tat gaa ata cca tca aaa gaa acc att agg ggc atc act<br>Pro His Thr Tyr Glu Ile Pro Ser Lys Glu Thr Ile Arg Gly Ile Thr<br>50                      55                    60 | 192 |
| cct tct cca tgc act gaa gct ttc ggg gca tgt ttt cat ggc aca tcc<br>Pro Ser Pro Cys Thr Glu Ala Phe Gly Ala Cys Phe His Gly Thr Ser<br>65                      70                    75                  80 | 240 |
| aac gac cat gtt ttt ttt ggc atg gcc tat acc acc cca cca act att<br>Asn Asp His Val Phe Phe Gly Met Ala Tyr Thr Thr Pro Pro Thr Ile<br>                  85                    90                  95 | 288 |
| gaa ccc aac gtt tca cat gtc tca cat gac aat act atg tgg gaa aac<br>Glu Pro Asn Val Ser His Val Ser His Asp Asn Thr Met Trp Glu Asn<br>                  100                 105               110 | 336 |
| gat caa aac caa gga ttc atc ttt gga acc gag tca acc ctc aat caa<br>Asp Gln Asn Gln Gly Phe Ile Phe Gly Thr Glu Ser Thr Leu Asn Gln<br>             115                 120               125 | 384 |
| gcc atg gcg gac tct aat caa ttc aat atg cca aaa cca ctc ttg agc<br>Ala Met Ala Asp Ser Asn Gln Phe Asn Met Pro Lys Pro Leu Leu Ser<br>130                   135               140 | 432 |
| gca aac gaa gac acc atc atg aat cga cgt caa aat aac cag gta atg<br>Ala Asn Glu Asp Thr Ile Met Asn Arg Arg Gln Asn Asn Gln Val Met<br>145                   150               155               160 | 480 |
| atc aag acc gag cag atc aag aag aag aac aag aga ttt cag atg agg<br>Ile Lys Thr Glu Gln Ile Lys Lys Lys Asn Lys Arg Phe Gln Met Arg<br>             165                 170               175 | 528 |
| agg ata tgt aaa ccc aca aaa aaa gct agc atc atc aaa gga caa tgg<br>Arg Ile Cys Lys Pro Thr Lys Lys Ala Ser Ile Ile Lys Gly Gln Trp<br>                  180                 185               190 | 576 |
| act cct gaa gaa gac aag tta ttg gtg cag cta gtg gac ctt cac gga<br>Thr Pro Glu Glu Asp Lys Leu Leu Val Gln Leu Val Asp Leu His Gly<br>             195                 200               205 | 624 |
| act aaa aaa tgg tct cag att gct aag atg ctt caa gga cga gtt gga<br>Thr Lys Lys Trp Ser Gln Ile Ala Lys Met Leu Gln Gly Arg Val Gly<br>210                   215               220 | 672 |
| aaa cag tgc aga gaa agg tgg cat aac cat ctc cgt ccc gat atc aag<br>Lys Gln Cys Arg Glu Arg Trp His Asn His Leu Arg Pro Asp Ile Lys<br>225                   230               235               240 | 720 |
| aaa gat gga tgg act gaa gaa gag gat ata ata ctg ata aaa gcc cat<br>Lys Asp Gly Trp Thr Glu Glu Glu Asp Ile Ile Leu Ile Lys Ala His<br>                  245                 250               255 | 768 |
| aag gag att ggg aac aga tgg gct gag ata gct cga aaa ctc ccg gga<br>Lys Glu Ile Gly Asn Arg Trp Ala Glu Ile Ala Arg Lys Leu Pro Gly<br>             260                 265               270 | 816 |
| cgc act gaa aat acg atc aag aac cat tgg aac gcg act aaa cgt cga<br>Arg Thr Glu Asn Thr Ile Lys Asn His Trp Asn Ala Thr Lys Arg Arg<br>             275                 280               285 | 864 |

```
caa cac tcg agg agg act aaa gga aaa gat gaa att tcc ctt tca ctt     912
Gln His Ser Arg Arg Thr Lys Gly Lys Asp Glu Ile Ser Leu Ser Leu
    290                 295                 300 ggt agc aac act ctt cag aac tac att agg tct gtt acc tac aat gat     960
Gly Ser Asn Thr Leu Gln Asn Tyr Ile Arg Ser Val Thr Tyr Asn Asp
305                 310                 315                 320 gat cct ttc atg acc gca aat gca aac gca aac att ggt cca aga aac    1008
Asp Pro Phe Met Thr Ala Asn Ala Asn Ala Asn Ile Gly Pro Arg Asn
                325                 330                 335 atg aga ggt aaa ggt aag aat gta atg gtt gcg gtc tcg gag tat gat    1056
Met Arg Gly Lys Gly Lys Asn Val Met Val Ala Val Ser Glu Tyr Asp
            340                 345                 350 gag ggt gaa tgt aag tat att gtg gat ggt gtg aat aac ttg ggt tta    1104
Glu Gly Glu Cys Lys Tyr Ile Val Asp Gly Val Asn Asn Leu Gly Leu
        355                 360                 365 gaa gat gga agg atc aag atg ccg tca ttg gcg gct atg tcg gcc tcc    1152
Glu Asp Gly Arg Ile Lys Met Pro Ser Leu Ala Ala Met Ser Ala Ser
370                 375                 380 gga tca gcg tct act tct ggt tct gcg tct ggt tct gga agt ggt gtg    1200
Gly Ser Ala Ser Thr Ser Gly Ser Ala Ser Gly Ser Gly Ser Gly Val
385                 390                 395                 400 acc atg gag att gat gag ccg atg act gat agc tgg atg gtg atg cat    1248
Thr Met Glu Ile Asp Glu Pro Met Thr Asp Ser Trp Met Val Met His
                405                 410                 415 gga tgt gat gaa gtt atg atg aac gag att gct ttg ctg gag atg att    1296
Gly Cys Asp Glu Val Met Met Asn Glu Ile Ala Leu Leu Glu Met Ile
            420                 425                 430 gct cat ggt cgt ctt tag                                             1314
Ala His Gly Arg Leu
        435

<210> SEQ ID NO 2
<211> LENGTH: 437
<212> TYPE: PRT
<213> ORGANISM: Arabidopsis thaliana

<400> SEQUENCE: 2

Met Glu Phe Glu Ser Val Phe Lys Met His Tyr Pro Tyr Leu Ala Ala
1               5                   10                  15

Val Ile Tyr Asp Asp Ser Ser Thr Leu Lys Asp Phe His Pro Ser Leu
            20                  25                  30

Thr Asp Asp Phe Ser Cys Val His Asn Val His Lys Pro Ser Met
        35                  40                  45

Pro His Thr Tyr Glu Ile Pro Ser Lys Glu Thr Ile Arg Gly Ile Thr
    50                  55                  60

Pro Ser Pro Cys Thr Glu Ala Phe Gly Ala Cys Phe His Gly Thr Ser
65                  70                  75                  80

Asn Asp His Val Phe Phe Gly Met Ala Tyr Thr Thr Pro Thr Ile
                85                  90                  95

Glu Pro Asn Val Ser His Val Ser His Asp Asn Thr Met Trp Glu Asn
            100                 105                 110

Asp Gln Asn Gln Gly Phe Ile Phe Gly Thr Glu Ser Thr Leu Asn Gln
        115                 120                 125

Ala Met Ala Asp Ser Asn Gln Phe Asn Met Pro Lys Pro Leu Leu Ser
    130                 135                 140

Ala Asn Glu Asp Thr Ile Met Asn Arg Arg Gln Asn Asn Gln Val Met
145                 150                 155                 160
```

```
Ile Lys Thr Glu Gln Ile Lys Lys Asn Lys Arg Phe Gln Met Arg
                165                 170                 175

Arg Ile Cys Lys Pro Thr Lys Lys Ala Ser Ile Ile Lys Gly Gln Trp
            180                 185                 190

Thr Pro Glu Glu Asp Lys Leu Leu Val Gln Leu Val Asp Leu His Gly
        195                 200                 205

Thr Lys Lys Trp Ser Gln Ile Ala Lys Met Leu Gln Gly Arg Val Gly
    210                 215                 220

Lys Gln Cys Arg Glu Arg Trp His Asn His Leu Arg Pro Asp Ile Lys
225                 230                 235                 240

Lys Asp Gly Trp Thr Glu Glu Asp Ile Ile Leu Ile Lys Ala His
                245                 250                 255

Lys Glu Ile Gly Asn Arg Trp Ala Glu Ile Ala Arg Lys Leu Pro Gly
                260                 265                 270

Arg Thr Glu Asn Thr Ile Lys Asn His Trp Asn Ala Thr Lys Arg Arg
                275                 280                 285

Gln His Ser Arg Arg Thr Lys Gly Lys Asp Glu Ile Ser Leu Ser Leu
        290                 295                 300

Gly Ser Asn Thr Leu Gln Asn Tyr Ile Arg Ser Val Thr Tyr Asn Asp
305                 310                 315                 320

Asp Pro Phe Met Thr Ala Asn Ala Asn Ala Asn Ile Gly Pro Arg Asn
                325                 330                 335

Met Arg Gly Lys Gly Lys Asn Val Met Val Ala Val Ser Glu Tyr Asp
                340                 345                 350

Glu Gly Glu Cys Lys Tyr Ile Val Asp Gly Val Asn Asn Leu Gly Leu
            355                 360                 365

Glu Asp Gly Arg Ile Lys Met Pro Ser Leu Ala Ala Met Ser Ala Ser
        370                 375                 380

Gly Ser Ala Ser Thr Ser Gly Ser Ala Ser Gly Ser Gly Ser Gly Val
385                 390                 395                 400

Thr Met Glu Ile Asp Glu Pro Met Thr Asp Ser Trp Met Val Met His
                405                 410                 415

Gly Cys Asp Glu Val Met Met Asn Glu Ile Ala Leu Leu Glu Met Ile
                420                 425                 430

Ala His Gly Arg Leu
            435

<210> SEQ ID NO 3
<211> LENGTH: 34
<212> TYPE: DNA
<213> ORGANISM: Artificial
<220> FEATURE:
<223> OTHER INFORMATION: PCR primer

<400> SEQUENCE: 3 ataggcgcg ccatggagtt cgagtcagtg ttca                            34

<210> SEQ ID NO 4
<211> LENGTH: 33
<212> TYPE: DNA
<213> ORGANISM: Artificial
<220> FEATURE:
<223> OTHER INFORMATION: PCR primer

<400> SEQUENCE: 4
aataactagt ctaaagacga ccatgagcaa tca                            33
```